US009050337B2

(12) United States Patent
Kim

(10) Patent No.: US 9,050,337 B2
(45) Date of Patent: Jun. 9, 2015

(54) METHOD FOR TREATING ATROPHIC SKIN SCARS USING A MIXTURE OF BOTULINUM TOXIN AND AIR

(76) Inventor: Sang Duck Kim, Seoul (KR)

( * ) Notice: Subject to any disclaimer, the term of this patent is extended or adjusted under 35 U.S.C. 154(b) by 0 days.

(21) Appl. No.: 14/114,443

(22) PCT Filed: Jun. 26, 2012

(86) PCT No.: PCT/KR2012/005029
§ 371 (c)(1),
(2), (4) Date: Jan. 7, 2014

(87) PCT Pub. No.: WO2013/002531
PCT Pub. Date: Jan. 3, 2013

(65) Prior Publication Data
US 2014/0127186 A1     May 8, 2014

Related U.S. Application Data

(60) Provisional application No. 61/501,624, filed on Jun. 27, 2011.

(51) Int. Cl.
    *A61K 38/48*     (2006.01)
    *A61K 9/00*     (2006.01)
    *A61K 9/12*     (2006.01)

(52) U.S. Cl.
    CPC ........... *A61K 38/4893* (2013.01); *A61K 9/0014* (2013.01); *A61K 9/12* (2013.01)

(58) Field of Classification Search
USPC .................................. 424/94.67, 239.1, 449
See application file for complete search history.

(56) References Cited

U.S. PATENT DOCUMENTS

| 6,447,787 | B1 * | 9/2002 | Gassner et al. | ............. 424/247.1 |
| 2012/0135937 | A1 * | 5/2012 | Bertholon et al. | ............. 514/18.8 |
| 2012/0189586 | A1 * | 7/2012 | Harrell | ......................... 424/93.7 |

FOREIGN PATENT DOCUMENTS

| KR | 10-2001-0089347 A | 10/2001 |
| KR | 10-2006-0133042 A | 12/2006 |
| KR | 10-2008-0071615 A | 8/2008 |
| KR | 10-2011-0033243 A | 3/2011 |

OTHER PUBLICATIONS

Berman B. et al. Novel Opportunities in the Treatment and Prvention of Scarring. J of Cutaneous Medicine and Surgery 8(Suppl 3)32-36, 2004.*
Lee B. et al. Effect of Botulinum Toxin Type A on a Rat Surgical Wound Model. Clinical Experimental Otorhinolaryngology 2(1)20-27, Mar. 2009.*
Wilson A. et al. Eradication of Keloids. Canadian J Plastic Surgery 21(2)87-91, May 17, 2013.*
Bennett M. et al. Introduction to Cosmetic Dermatology. Current Problems in Dermatology US 15(2)43-83, Mar.-Apr. 2003.*
Liu A. et al. Current Methods Employed in the Prevention and Minimization of Surgical Scars. Dermatologic Surgery 37(12)1740-1746, Dec. 2011.*
Wilson A. et al. Eradication of Keloids. Canadian J Plastic Surgery 21(2)87-91, Summer May 17, 2013.*
Xiao et al., "Effect of Botulinum Toxin Type A on Transforming Growth Factor β1 in Fibroblasts Derived from Hypertrophic Scar: A Preliminary Report", Aesthetic Plastic Surgery, vol. 34, No. 4, pp. 424-427 (2010).
Zhibo et al., "Intralesional Botulinum Toxin Type A Injection as a New Treatment Measure for Keloids", Plastic and Reconstrucive Surgery, vol. 124, No. 5, pp. 275e-277e (2009).

* cited by examiner

*Primary Examiner* — Ralph Gitomer
(74) *Attorney, Agent, or Firm* — Bret E. Field; Bozicevic, Field & Francis LLP

(57) ABSTRACT

The present invention relates to a pharmaceutical composition for treating scars on the skin, comprising a mixture of botulinum toxin and air. The mixture of botulinum toxin and air according to the present invention, when injected in the dermis, may temporarily removed the elasticity of the dermis and flatten out the depressed part of the scar, and thus enables elaborate intradermic resection and increases the therapeutic effects of lasers for treating pulsed dye laser or of fractional lasers. Thus, scars on the skin can be effectively improved through a one-time operation without negatively affecting the daily lives of patients.

4 Claims, 4 Drawing Sheets

Fig. 4

Change in numerical values of depressed
scars in control group (air)

Before treatment　　　　　After treatment

Change in numerical values of depressed
scars in mixture of botulinum toxin and air Before treatment　　　　　After treatment

METHOD FOR TREATING ATROPHIC SKIN SCARS USING A MIXTURE OF BOTULINUM TOXIN AND AIR

This application is a national stage application filed under Rule 371 based on PCT/KR2012/005029 filed Jun. 26, 2012 which claims benefit of 61/501,624 filed Jun. 27, 2011.

FIELD OF THE INVENTION

The present invention relates to a pharmaceutical composition for treating skin scars, comprising a mixture of botulinum toxin and air, and a method for treating skin scars using the same.

BACKGROUND

Skin protects the body's organs from external environmental threats and acts as a thermostat to maintain body temperature. The skin consists of several different layers, each with a specialized function. The major layers include the epidermis, the dermis and the hypodermis. The epidermis is a stratifying layer of epithelial cells that overlies the dermis, which consists of connective tissue. Both the epidermis and the dermis are further supported by the hypodermis, an internal layer of adipose tissue.

The epidermis, the topmost layer of skin, is only 0.1 to 1.5 millimeters thick (Inlander, Skin, New York, N.Y.: People's Medical Society, 1-7 (1998)). It consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the water-holding capacity of keratin. When the stratum corneum loses its softness and flexibility, it becomes rough and brittle, resulting in dry skin. The dermis, which lies just beneath the epidermis, is 1.5 to 4 millimeters thick. It is the thickest of the three layers of the skin. In addition, the dermis is also home to most of the skin's structures, including sweat and oil glands (which secrete substances through openings in the skin called pores, or comedos), hair follicles, nerve endings, and blood and lymph vessels (Inlander, Skin, New York, N.Y.: People's Medical Society, 1-7 (1998)). However, the main components of the dermis are collagen and elastin. The hypodermis is the deepest layer of the skin. It acts both as an insulator for body heat conservation and as a shock absorber for organ protection (Inlander, Skin, New York, N.Y.: People's Medical Society, 1-7 (1998)). In addition, the hypodermis also stores fat for energy reserves. The pH of skin is normally between 5 and 6. This acidity is due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's stratum corneum.

Botulinum toxins (also known as botulin toxins or botulinum neurotoxins) are neurotoxins produced by the gram-positive bacteria *Clostridium botulinum*. They act to produce paralysis of muscles by preventing synaptic transmission or release of acetylcholine across the neuromuscular junction, and are thought to act in other ways as well. Their action essentially blocks signals that normally would cause muscle spasms or contractions, resulting in paralysis. Botulinum toxin is classified into eight neurotoxins that are serologically related, but distinct. Of these, seven can cause paralysis, namely botulinum neurotoxin serotypes A, B, C, D, E, F and G. Each of these is distinguished by neutralization with type-specific antibodies. Nonetheless, the molecular weight of the botulinum toxin protein molecule, for all seven of these active botulinum toxin serotypes, is about 150 kD. The botulinum toxins released by the bacterium are complexes comprising the 150 kD botulinum toxin protein molecule in question along with associated non-toxin proteins. The botulinum toxin type A complex can be produced by Clostridia bacterium as 900 kD, 500 kD and 300 kD forms. Botulinum toxin types B and C are apparently produced as only a 700 kD or 500 kD complex. Botulinum toxin type D is produced as both 300 kD and 500 kD complexes. Botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg, about 12 times the primate $LD_{50}$ for type A. Due to the molecular size and molecular structure of botulinum toxin, it cannot cross the stratum corneum and the multiple layers of the underlying skin architecture.

Botulinum toxin type A is said to be the most lethal natural biological agent known to man. Spores of *C. botulinum* are found in soil and can grow in improperly sterilized and sealed food containers. Ingestion of the bacteria can cause botulism, which can be fatal.

Meanwhile, a scar is a mark left on the skin after it heals, and in particular, a depressed scar is a pathological response of the skin such as dermal damage or fibrosis after an injury of the epidermis. Treatment methods of depressed scars include dermabrasion for removing the skin layer of damaged area using laser irradiation or various compounds or using a dermabrator, subcision (elevating the bottom of the dermis) for increasing the height of the depressed scar. However, in the case of dermabrasion, it affects the daily life, and the effect of filling the scar is reduced, and in the case of subcision, the effect of precisely adjusting the height of the scar is reduced due to fibrosis on the boundary of the scar, leading to unsatisfactory cosmetic results after surgical procedure.

The muscle-paralyzing effects of botulinum toxin have been used for therapeutic effects on various conditions such as hemifacial spasm, adult onset spasmodic torticollis, anal fissure, blepharospasm, cerebral palsy, cervical dystonia, migraine headaches, strabismus, temperomandibular joint disorder, and various types of muscle cramping and spasms. More recently, the muscle-paralyzing effects of botulinum toxin have been taken advantage of in therapeutic and cosmetic facial applications such as treatment of wrinkles, frown lines, and other results of spasms or contractions of facial muscles. However, no research on the treatment of scars using botulinum toxin has been reported, and in particular, no method for effectively treating skin scars by preparing botulinum toxin in the form of a mixture and injecting the mixture in a skin-specific manner has been reported.

Therefore, if the problems of existing scar treatment methods can be solved using botulinum toxins which have been used in the treatment of various diseases, the botulinum toxin can be effectively used in the treatment of skin scars, and thus research on a new composition for treating skin scars using botulinum toxin and a method for treating skin scars is urgently required.

SUMMARY

Technical Problem

The present inventors have studied methods for treating skin scars using botulinum toxin and found that when a mixture of botulinum toxin and air is injected into the dermis, it removes the elasticity of the dermis and elevates a depressed scar to effectively increase the effect of treating skin scars, thus completing the present invention.

Therefore, an object of the present invention is to provide a pharmaceutical composition for treating skin scars, comprising a mixture of botulinum toxin and air, and a method for treating skin scars using the same.

Technical Solution

To achieve the above object, the present invention provides a pharmaceutical composition for treating skin scars, comprising a mixture of botulinum toxin and air.

Another object of the present invention is to provide a method for treating skin scars, comprising injecting the composition into the dermis.

Advantageous Effects

According to the mixture of botulinum toxin and air of the present invention, when it is injected into the dermis, the elasticity of the dermis is temporarily removed and the depressed scar is elevated, which allows subcision to be precisely performed and increases the therapeutic effect of pulsed dye laser or fractional laser, thus effectively treating skin scars with only one surgical procedure without affecting the daily life.

BRIEF DESCRIPTION OF THE DRAWINGS

FIG. 4 is a diagram showing the comparison of the effects of treating skin scars depending on the mixture ratio of botulinum toxin and air (volume ratios of 1:1, 1:2, and 1:3).

DETAILED DESCRIPTION

Figure 1:
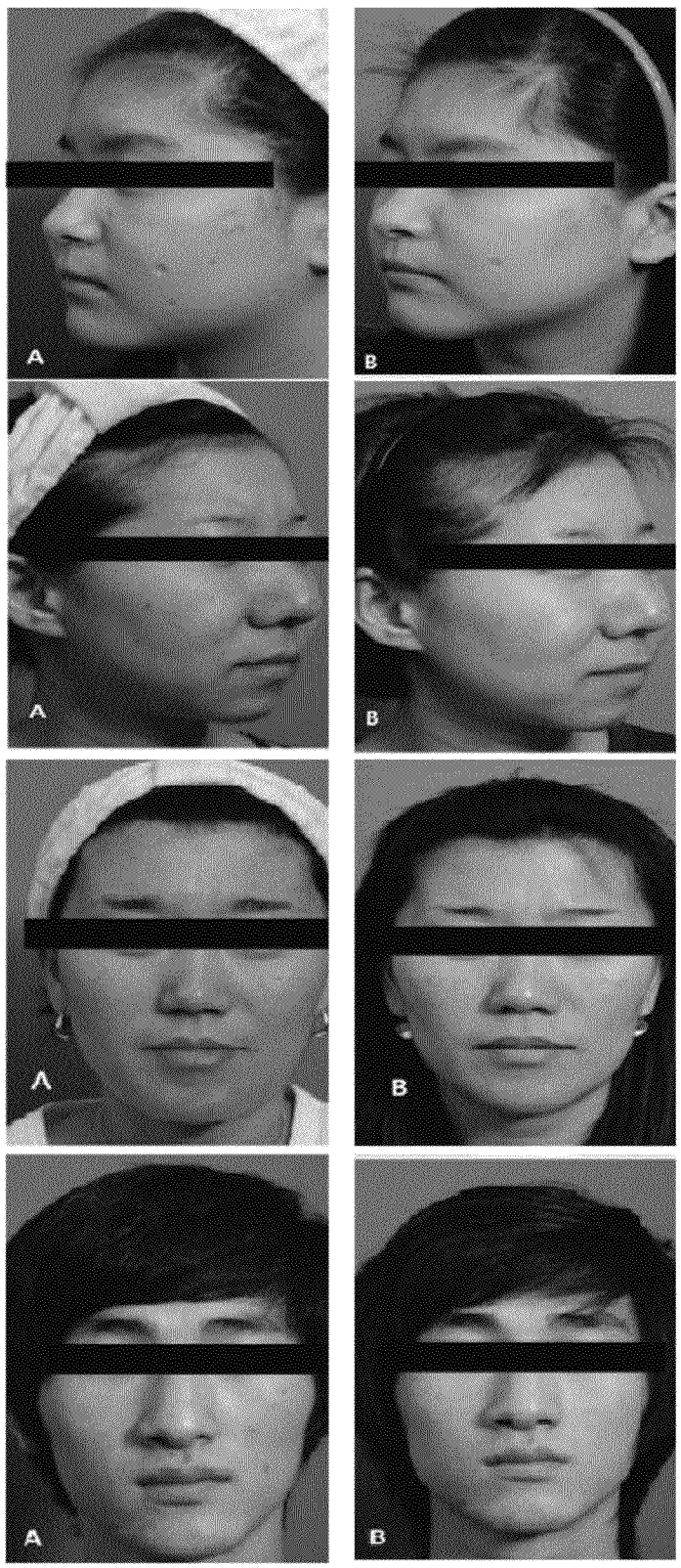
FIG. 1 is a diagram showing the comparison of the effects of treating skin scars before surgical procedure (A) and 6 months after injecting a composition of the present invention and performing subcision once (B).

The present invention provides a pharmaceutical composition for treating skin scars, comprising a mixture of botulinum toxin and air.

When the mixture of botulinum toxin and air is injected into the dermis, the elasticity of the dermis is temporarily removed and the depressed scar is elevated, which allows subcision to be precisely performed and increases the therapeutic effect of pulsed dye laser or fractional laser, thus effectively treating skin scars with only one surgical procedure without affecting the daily life.

In the present invention, the term "botulinum toxin" refers to a molecule that has the biological activity of botulinum toxin and may be a protein, polypeptide, peptide, fusion protein, truncated protein, chimeric protein, mutant protein, or recombinant protein.

The biological activity of the toxin refers, within the context of the present invention, to muscular paralysis or inhibition of exocytosis, in particular, inhibition of exocytosis of acetylcholine or other neurotransmitters.

Pure or substantially pure botulinum neurotoxin can be obtained from a protein complex containing botulinum toxin, for example according to the method described in the literature (Current topics in Microbiology and Immunology (1995), 195, p. 151-154). Pure or substantially pure botulinum neurotoxin can be obtained, for example, by purification of a fermentation medium or culture broth containing *Clostridium botulinum* strain and can be enriched, for example, with meat or protein-rich food.

The botulinum toxin may comprise at least one selected from the group consisting of botulinum toxin serotypes A, B, C, D, E, F and G and may comprise both Dysport® and Botox®, botulinum neurotoxin Type A products without limitation. Moreover, Myoblock®, a botulinum toxin Type B product, may be included in the botulinum toxin.

The botulinum toxin and air may be mixed in a volume ratio of 1:0.1 to 1:10 to prepare a pharmaceutical composition for treating skin scars and may preferably be mixed in a volume ratio of 1:2 to 1:4.

The composition of the present invention may be used in various forms for the treatment of scars and may be used for pretreatment of subcision for the purpose of removing the elasticity of the dermis and elevating the depressed scar.

The composition of the present invention may further comprise appropriate carrier, excipient, and diluent which are generally used in the preparation of pharmaceutical compositions.

The composition of the present invention may preferably be formulated in the form of liquid, aerosol, and sterile injection, and most preferably, the mixture of botulinum toxin and air may be formulated in the form of aerosol. When the composition is formulated, diluents or excipients such as fillers, extenders, binders, wetting agents, disintegrants, surfactants, etc. may be used.

The composition of the present invention may optionally comprise a dispersant. As used herein, the dispersant refers to any substance or additive capable of preventing or minimizing undesired or uncontrolled agglomeration between the botulinum toxin and the carrier of the present invention. The dispersant is useful when a concentrated botulinum toxin solution is to be employed due to capacity limit, for example. In these cases, the dispersant allows the botulinum toxin to be dispersed, thus preventing the agglomeration of toxins which may occur in the absence of the dispersant. In general, the dispersant (1) is non-irritating, (2) does not destroy the botulinum toxin, (3) does not cause an increase in permeability, (4) has a reliable and stable particle size, (5) does not have a charge, and (6) does not interfere with complexes of toxins and transdermal carriers.

The injection of the present invention refers to the administration of a predetermined composition of the present invention to a subject by any suitable route.

The preferred dosage of the pharmaceutical composition of the present invention depends on the scar condition and weight of a patient, the severity of disease, the type of drug, the route and duration of administration, etc., but may be appropriately selected by those skilled in the art. For the desired effect, the composition of the present invention may be administered in an amount of 0.1 unit to 3000 units per injection, preferably 1 unit to 10 units, based on the content of botulinum toxin type A. The composition of the present invention may be administered once or several times a day.

The composition of the present invention may be used alone or in conjunction with surgery, radiation therapy, hormone therapy, chemical therapy, and methods using biological response modifiers for the treatment of skin scars and may preferably be used in conjunction with pulsed dye laser or fractional laser, and subcision.

Moreover, the present invention provides an aerosol spray kit comprising the composition formulated in the form of aerosol.

The present invention provides a kit comprising a device for injection the botulinum toxin into the skin as well as a liquid, gel, cream, etc. suitable for use in the skin or epithelium of a subject. The kit for administration of the composition of the present invention under the instructions of a medical practitioner or by a patient or subject may comprise a custom applicator suitable for its purpose.

Moreover, the present invention provides a method for treating skin scars, comprising the steps of:

(1) removing the elasticity of the dermis of wounded skin by injecting a mixture of botulinum toxin and air into the dermis through a syringe needle of 28 gauge to 31 gauge; and (2) performing at least one surgical procedure selected from the group consisting of subcision, pulsed dye laser, and fractional laser on the dermis whose elasticity is removed in step (1).

The method of the present invention will be described in more detail step by step.

Step (1) is to remove the elasticity of the dermis of wounded skin by injecting a mixture of botulinum toxin and air, in which the botulinum toxin and air are mixed in a volume ratio of 1:0.1 to 1:10, preferably 1:2 to 1:4 and injected into a depressed scar of a subject's skin.

The injection may be performed by administering the mixture using a syringe needle of 28 gauge to 31 gauge, and the mixture may preferably be sprayed through a syringe needle of 31 gauge and may be sprayed and injected into the skin scar at a very high pressure by Bernoulli's fluid dynamics. Moreover, a BD insulin syringe with a syringe needle of 28 gauge to 31 gauge may be used.

The injection may preferably be performed by spraying the composition in the form of aerosol.

Step (2) is to additionally perform at least one surgical procedure selected from the group consisting of subcision, pulsed dye laser, and fractional laser after injecting the mixture of botulinum toxin and air.

The subcision may be performed on the dermis whose elasticity is temporarily removed by injecting the mixture of step (1), thus precisely adjusting the height of the scar.

The pulsed dye laser or fractional laser may have a synergistic effect on the treatment of skin scars together with the therapeutic effect of the mixture of botulinum toxin and air.

EXAMPLES

Hereinafter, the present invention will be described in detail with reference to Examples. However, the following Examples are merely illustrative of the present invention and the present invention is not limited by the following Examples.

Example 1

Preparation of Composition Mixed with Botulinum Toxin and Air 0.5 U/cc botulinum toxin solution was prepared by adding 10 cc saline solution to a bottle containing 50 U Botox, a botulinum toxin Type A1, and diluting the resulting mixture. The prepared botulinum toxin solution was loaded in a BD Ultra-Fine™ II Short Needle Insulin Syringe 3/10 cc 31 G×8 mm (5/16 in), and the atmospheric air was filled in the corresponding syringe to prepare a mixture of botulinum toxin and air. At this time, the botulinum toxin and air were mixed in a volume ratio of 1:1, 1:2, 1:3, and 1:4, respectively.

In order to compare the effects of the prepared compositions on the treatment of scars, control groups treated with air only and treated with botulinum toxin only were established in the following Examples.

Example 2

Determination of Treatment of Skin Scars

The composition (mixed with 0.03 cc botulinum toxin and 0.12 cc air) prepared in Example 1 was administered to the dermis of five patients with actual scars, and the subcision was performed to determine the effects of treating skin scars. The subcision was performed once or three times, and the appearance of skin scars after 6 months from the subcision was compared to the appearance of skin scars before the subcision.

Figure 2:
FIG. 2 is a diagram showing the comparison of the effects of treating skin scars before surgical procedure (A) and 6 months after injecting a composition of the present invention and performing subcision three times (B).
Figure 2:
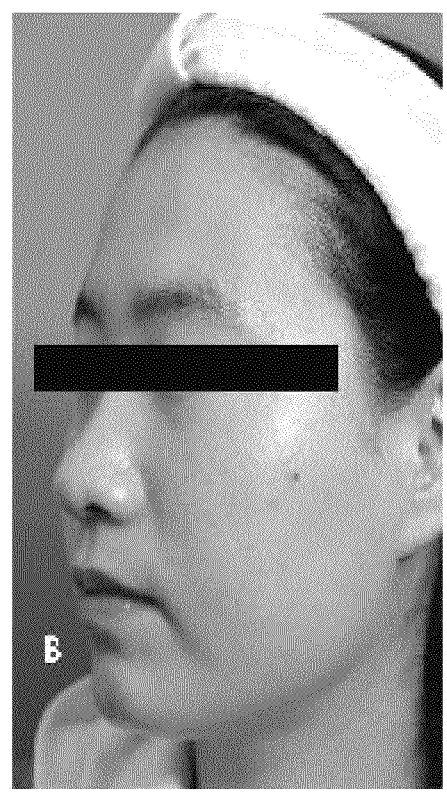

The results are shown in FIGS. 1 and 2.

As shown in FIGS. 1 and 2, as a result of performing the method for treating skin scar according to the present invention, all patients with skin scars showed significant therapeutic effects, and the treatment satisfaction was more than 80% with only one surgical procedure, indicating that the patients' satisfaction was very high.

Example 3

Figure 3:
FIG. 3 is a diagram showing depressed scars in five areas on the left and right faces of a patient.

Comparison of Effects of Treating Skin Scars Depending on the Mixture Ratio of Botulinum Toxin and Air In order to numerically determine the effects of treating skin scar, which were determined with the naked eye in Example 2, atmospheric air containing no botulinum toxin, botulinum toxin containing no air, and compositions mixed with botulinum toxin and air in volume ratios of 1:1, 1:2 and 1:3 were injected into patient's atrophic scars, which were then treated with pulsed dye laser and fractional laser. More specifically, in order to eliminate analytical errors due to individual differences in the restoration of scars, five depressed scar areas were selected from the left and right faces of each patient (FIG. 3), the mixed compositions were injected into the corresponding areas, and the effects of treating scars were quantified. For the quantification of the degree of treating depressed scars, the 3D LifeViz II™ (Quantificare, France) for numerically measuring the face by three-dimensional analysis was used.

The results are shown in FIG. 4 and Table 1.

TABLE 1

| BTX (Botulinum toxin) | | AT (Air) | | BTX:AT = 1:1 | | BTX:AT = 1:2 | | BTX:AT = 1:3 | |
|---|---|---|---|---|---|---|---|---|---|
| Perimeter | 38.53 | Perimeter | 39.8 | Perimeter | 34.63 | Perimeter | 32.86 | Perimeter | 35.79 |
| Surface | 85.5 | Surface | 75.72 | Surface | 69.62 | Surface | 54.18 | Surface | 66.54 |
| Volume | 307.8 | Volume | 124.36 | Volume | 79.99 | Volume | 57.1 | Volume | 132.13 |
| Volume > 0 | 307.8 | Volume > 0 | 124.36 | Volume > 0 | 79.99 | Volume > 0 | 57.1 | Volume > 0 | 132.13 |
| Volume < 0 | 0 | Volume < 0 | 0 | Volume < 0 | 0 | Volume < 0 | 0 | Volume < 0 | 0 |
| Av Deep | 3.6 | Av Deep | 1.64 | Av Deep | 1.15 | Av Deep | 1.05 | Av Deep | 1.99 |
| Minimum | 0 | Minimum | 0 | Minimum | 0 | Minimum | 0 | Minimum | 0 |
| Maximum | 0 | Maximum | 0 | Maximum | 0 | Maximum | 0 | Maximum | 0 |
| Rugosity | 3.6 | Rugosity | 1.64 | Rugosity | 1.15 | Rugosity | 1.05 | Rugosity | 1.99 |
| After treatment | | | | | | | | | |
| Perimeter | 40.02 | Perimeter | 36.03 | Perimeter | 42.67 | Perimeter | 39.26 | Perimeter | 38.18 |
| Surface | 82.73 | Surface | 59.68 | Surface | 95.82 | Surface | 83.55 | Surface | 82.42 |
| Volume | 340.78 | Volume | 135.3 | Volume | 185.68 | Volume | 204.93 | Volume | 209.04 |
| Volume > 0 | 340.78 | Volume > 0 | 135.3 | Volume > 0 | 185.68 | Volume > 0 | 204.93 | Volume > 0 | 209.04 |
| Volume < 0 | 0 | Volume < 0 | 0 | Volume < 0 | 0 | Volume < 0 | 0 | Volume < 0 | 0 |
| Av Deep | 4.12 | Av Deep | 2.27 | Av Deep | 1.94 | Av Deep | 2.45 | Av Deep | 2.54 |
| Minimum | 0 | Minimum | 0 | Minimum | 0 | Minimum | 0 | Minimum | 0 |
| Maximum | 0 | Maximum | 0 | Maximum | 0 | Maximum | 0 | Maximum | 0 |
| Rugosity | 4.12 | Rugosity | 2.27 | Rugosity | 1.94 | Rugosity | 2.45 | Rugosity | 2.54 |
| Volume increase rate | 1.107147498 | | 1.087970408 | | 2.321290161 | | 3.588966725 | | 1.582078256 |

As shown in FIG. 4, the difference in the numerical values of the depressed scars treated with atmospheric air alone as the control and treated with the mixture of botulinum toxin and air could be determined using the 3D LifeViz II™. In particular, as shown in table 1, the comparison of the elevations of depressed scars treated with the compositions mixed with botulinum toxin and air in volume ratios of 1:1, 1:2 and 1:3 and those of the control groups showed that the increase in the volume ratio in the control group treated with botulinum toxin alone was 1.0, and that in the control group treated with air alone was 1.1, indicating that there was almost no effect of treating depressed scars. However, in the case of the compositions mixed with botulinum toxin and air, the increase in the volume ratio was 1.5 times to 3.5 times, which meant that the depressed scars were elevated within a short time, indicating that there were significant effects of treating skin scars.

Hereinafter, formulation examples for the composition of the present invention will be illustrated.

Formulation Example 1

Pharmaceutical Composition 1.1 Preparation of Injection

| | |
|---|---|
| Mixture of botulinum toxin and air of the present invention | 10 mg |
| Mannitol | 180 mg |
| Sterile distilled water for injection | 2974 mg |
| Na$_2$HPO$_4$•2H$_2$O | 26 mg |

An injection is prepared with the above ingredients per ampoule (2 ml) according to a conventional method for preparing injections.

1.2 Preparation of Liquid Formulation

| | |
|---|---|
| Mixture of botulinum toxin and air of the present invention | 10 mg |
| Isomerized sugar | 10 g |
| Mannitol | 5 g |
| Purified water | Proper quantity |

A liquid formulation is prepared according to a conventional method for preparing liquid formations by dissolving each ingredient in purified water, adding a proper quantity of lemon flavor, mixing the ingredients, adding purified water to the resulting mixture to regulate the total mixture to 100 ml, filling the mixture in a brown bottle, and sterilizing the mixture.

The invention claimed is:

1. A method for treating an atrophic skin scar, the method comprising the steps of:
   (1) removing the elasticity of the atrophic skin scar by injecting a mixture of botulinum toxin and air mixed in a volume ratio of 1:1 to 1:10 into the atrophic skin scar through a syringe needle of 28 gauge to 31 gauge; and
   (2) performing at least one surgical procedure selected from the group consisting of subcision, pulsed dye laser, and fractional laser on the atrophic skin scar whose elasticity is removed in step (1).

2. The method of claim 1, wherein a depressed area of the atrophic skin scar is elevated by the injection of step (1).

3. The method of claim 1, wherein the injection of step (1) is performed by spraying the composition in the form of aerosol.

4. The method of claim 1, wherein the procedure comprises subcision, and performing subcision comprises performing subcision on dermis whose elasticity has been temporarily removed by the action of step (1).

* * * * *